United States Patent [19]

Collins

[11] Patent Number: 5,083,563
[45] Date of Patent: Jan. 28, 1992

[54] IMPLANTABLE AUTOMATIC AND HAEMODYNAMICALLY RESPONSIVE CARDIOVERTING/DEFIBRILLATING PACEMAKER

[75] Inventor: Kenneth A. Collins, Neutral Bay, Australia

[73] Assignee: Telectronics Pacing Systems, Inc., Englewood, Colo.

[21] Appl. No.: 481,364

[22] Filed: Feb. 16, 1990

[51] Int. Cl.$^5$ .................... A61N 1/39; A61N 1/365
[52] U.S. Cl. ................ 128/419.00 D; 128/419.0 PG
[58] Field of Search ............... 128/419 PG, 672, 673, 128/419 D

[56] References Cited

U.S. PATENT DOCUMENTS

| | | | |
|---|---|---|---|
| 3,400,709 | 9/1968 | Funfstuck | 128/672 |
| 3,614,955 | 10/1971 | Mirowski et al. | 128/419 D |
| 3,650,277 | 3/1972 | Sjostrand et al. | 128/421 |
| 3,716,059 | 2/1973 | Welborn et al. | 128/419 D |
| 3,893,452 | 7/1975 | Birnbaum | 128/673 |
| 3,942,536 | 3/1976 | Mirowski et al. | 128/419 D |
| 4,023,563 | 5/1977 | Reynolds et al. | 128/672 |
| 4,080,966 | 3/1978 | McNally et al. | 128/673 |
| 4,161,173 | 7/1979 | Crestas et al. | 128/672 |
| 4,291,699 | 9/1981 | Geddes et al. | 128/419 D |
| 4,702,253 | 10/1987 | Nappholz et al. | 128/419 PG |
| 4,770,177 | 9/1988 | Schroeppel | 128/419 PG |
| 4,774,950 | 10/1988 | Cohen | 128/419 D |
| 4,791,931 | 12/1988 | Slate | 128/419 PG |
| 4,802,481 | 2/1989 | Schroeppel | 128/419 PG |
| 4,901,725 | 2/1990 | Nappholz et al. | 128/734 |
| 4,928,638 | 5/1990 | Mower | 128/419 PG |
| 4,940,053 | 7/1990 | Mann et al. | 128/419 PG |
| 4,945,909 | 8/1990 | Fearnot et al. | 128/419 PG |

OTHER PUBLICATIONS

Cohen, T. J. et al., "Haemodynamic Responses to Rapid Pacing: A Model for Tachycardia Differentiation", Pace, vol. 11, pp. 1522-1528 (1988).
Goldreyer, B. N., "Physiologic Pacing: The Role of AV Synchrony", Pace, vol. 5, pp. 613-615 (1982).
Khoury, D. et al., "Continuous Right Ventricular Volume Assessment by Catheter Measurement of Impedance for Anti-Tachycardia System Control", Pace, vol. 12, pp. 1918-1926 (1989).
Nakano, J., "Effects of Atrial and Ventricular Tachycardias on the Cardiovascular System", Am. J. Physiol. 206, pp. 547-552 (1964).
Guyton, A. C., "Textbook of Medical Physiology", 7th Edition, W. B. Saunders Company, pp. 150-164 (1986).
Wish, M. et al., "Importance of Left Atrial Timing in the Programming of Dual-Chamber Pacemakers", Am. J. Cardiol. 66, pp. 566-571 (1987).

*Primary Examiner*—William E. Kamm
*Assistant Examiner*—Kennedy J. Schaetzle
*Attorney, Agent, or Firm*—Gottlieb, Rackman & Reisman

[57] ABSTRACT

A cardioverting/defibrillating pacemaker with the ability to sense and respond to haemodynamic compromise. The ventricular pressure (VP) and electrical activity of the heart are sensed via one or more transvenous or epicardial devices. The filtered peak-to-peak amplitude (VFPPA) or a peak pressure function (VPPF) based upon the right and/or left VP waveform(s) are derived. In one embodiment the VP and the electrical activity of the heart are sensed and processed continuously, and the VFPPA or the VPPF continuously derived. The VFPPA or the VPPF, and the ECG are used to initiate bradycardia pacing, antitachycardia pacing and cardioversion/defibrillation therapies. In another embodiment the VP and electrical activity of the heart are continuously sensed. The electrical activity is processed continuously and used to determine whether or not some irregularity exists. If so, one of the VPPF or VFPPA is derived and used to decide which of the therapies are to be used. One of the VPPF or VFPPA is also periodically determined to ensure optimal haemodynamic function. In both emobidments the degree of haemodynamic compromise is determined by comparing the derived VFPPA or VPPF with programmed values. An algorithm maximizes the effectiveness of support pacing. Preferably an ECG transvenous sensor in the right atrium and a combined ECG/VP sensor in the right ventricle are used.

28 Claims, 6 Drawing Sheets

Typical Rate, RVPPF And RVFPPA Values During Arrhythmias (Rate Expressed As Beats Per Minute. RVPPF And RVFPPA Expressed As A Percentage Of Resting Values).

| Rate | RVPPF | RVFPPA | Therapy |
|---|---|---|---|
| <=120 | >60% | >80% | Normal Pacing Therapy |
| <=120 | <60% | <80% | Pacing Optimising Algorithm |
| >120 | >50% | >50% | Antitachycardia Pacing |
| >120 | >30% & <=50% | >30% & <=50% | Cardioversion |
| >120 | <=30% | <=30% | Defibrillation |

IMPLANTABLE AUTOMATIC AND HAEMODYNAMICALLY RESPONSIVE CARDIOVERTING/DEFIBRILLATING PACEMAKER

BACKGROUND OF THE INVENTION

1. Field of the Invention

This invention relates to implantable cardioverting and defibrillating pacemakers. More particularly it relates to an apparatus that adds the ability to transduce haemodynamic compromise to a cardioverting/defibrillating pacemaker.

2. Background Art

Pacemakers were initially developed to electrically stimulate hearts that were unable to beat at a rate sufficient to maintain a life sustaining cardiac output. The first devices delivered electrical stimuli at a fixed rate regardless of the heart's function or the body's physiological needs.

Devices were then developed that stimulated the heart only if it failed to beat above a predetermined rate. Such devices sensed the electrical activity of the heart, usually in the right ventricle. Later developments saw the introduction of pacemakers that sensed and stimulated in both the right atrium and the right ventricle.

Pacemakers were also introduced that obtain a measure of the body's physiological need and that responded by altering the paced rate to meet the demand, for example, by sensing the respiratory rate and then increasing the heart rate as the respiratory rate increased. Such a pacemaker is disclosed in U.S. Pat. No. 4,702,253 to Nappholz et al.

Devices were developed that electrically sensed the presence of a ventricular tachyarrhythmia and delivered a defibrillating D.C. shock to revert the heart to a normal rhythm. More advanced devices were developed that attempted to pace hearts undergoing a supraventricular or ventricular tachyarrhythmia back into a normal rhythm. This technique is known as antitachycardia pacing.

Devices have been developed that can act both as pacemakers and as arrhythmia control systems. These devices are able to pace a heart that is beating too slowly, to cardiovert/defibrillate a heart, and to pace a heart undergoing a ventricular tachyarrhythmia, back into a normal rhythm. The Guardian device is such a device and is described in U.S. patent application Ser. No. 187,797, of R. Grevis and N. Gilli, filed Apr. 29, 1988, and entitled "Apparatus and Method for Controlling Multiple Sensitivities in Arrhythmia Control Systems Including Post-therapy Pacing Delay", now U.S. Pat. No. 4,940,054.

The Guardian device is a microcomputer based arrhythmia control system. It is able to be programmed to many different bradycardia pacing modes. A telemetric link is used to communicate with the physician. Variables such as the bradycardia support pacing rate and the atrio-ventricular (AV) delay can be programmed to suit the needs of the recipient of the device. However, such parameters can only be altered by a telemetric link. There is no provision for the device to adjust its programmed parameters in a learning response mode.

The use of a telemetric link allows not only the reprogramming of a device, but also the interrogation of a device by a clinician. Some devices are also fitted with vibrating warning devices to indicate to the patient certain error states of the device and/or malfunctions of the heart. The idea is to hasten the patient's presentation to the clinician to allow interrogation of the device.

Despite the above developments, there are still some limitations inherent in any device that relies solely upon the sensing of the electrical activity of the heart as its means of determining the state of cardiac function. Such devices can be confused by electrical noise induced in the sensing circuits and have difficulty distinguishing a supraventricular from a ventricular tachyarrhythmia. Furthermore they are not able to determine whether or not a tachyarrhythmia is haemodynamically compromising, regardless of its origin. There are differences in the haemodynamic effects of the different tachyarrhythmias as documented by Nakano in his article "Effects of Atrial and Ventricular Tachycardias on the Cardiovascular System." Am. J. Physiol 206: 547–552 (1964).

The result of these shortcomings is that recipients of cardioverter/defibrillators and cardioverting/defibrillating pacemakers may be subject to the inappropriate delivery of defibrillation therapy. Such therapy is not without risk of damage to the myocardium. Furthermore, unwarranted discharge of the device causes pain to the conscious patient, instilling great anxiety, as well as shortening the life of the batteries that power the device.

Haemodynamic compromise exists when there is either insufficient blood pressure or blood flow to meet the oxygen demands of the tissues of the body (See Guyton A., "Textbook of Medical Physiology", 7th Ed., Saunders 1986). It is a relative term since the amount of oxygen required varies with the level of activity, the level of consciousness, feeding etc.

Monitoring the blood pressure is an effective means, commonly used in clinical practice, to assess an individual's haemodynamic state. A fall in arterial blood pressure is associated first with a loss of consciousness, then with ischaemia of vital organs, and finally with death either acutely due to anoxic brain death or, in the longer term, with the failure of other vital organs.

The heart is a cyclical pump with a pulsatile output that is smoothed in the capacitance vessels to produce a steady capillary flow of oxygen rich blood to the tissues. Thus arterial blood pressure shows cyclical peaks and troughs; the systolic and diastolic pressures.

The ventricular pressure, likewise, cyclically increases and decreases and is a measure of an individual's haemodynamic state. A voltage proportional to this pressure can be obtained via a piezo-electric device affixed to the end of a permanently implanted transvenous and intracardiac lead. In such a device a pressure sensor acts as one arm of a resistive bridge and varies its resistance, and therefore the voltage across it, with the pressure applied to it. A voltage waveform can thereby be obtained that reflects the changes in ventricular pressure, and therefore haemodynamnic state, over time.

With respect to bradycardia support pacing, one of the common strategies of optimizing cardiac output for a patient is to alter the A-V delay and/or pacing rate of his pacemaker. The latter in particular is fraught with risk. The patient must be carefully monitored after such manipulations since the patient may be pushed into heart failure.

Wish et al. ("Importance of Left Atrial Timing in the Programming of Dual-Chamber Pacemakers," Am. J. Cardiol 60: 566–571 (1987)) have shown that stroke volume can be optimized by manipulating the A-V delay. The optimal value for the A-V delay varies from patient to patient and with the pacing mode used. The present strategy is to use electrophysiological studies to determine the best value of A-V delay. However such studies are not without risk and must be repeated as a patient's clinical status varies over time.

Mirowski et al., in U.S. Pat. Nos. 3,614,955 and 3,942,536 describe systems that sense heart function using the peak of the right ventricular pressure waveform. Devices of this kind, which have yet to be commercially implemented, suffer some obvious disadvantages.

Generally devices which monitor only the peak of the ventricular pressure waveform are unable to initiate antitachycardia pacing and to automatically optimize bradycardia support pacing. Additionally, such devices are designed to use the raw RVP waveform. The common implementation of such a device utilizes a piezoelectric transducer. If such a device is implemented, it suffers the wandering baseline associated with piezoelectric pressure transducers and an inability to respond to alterations in a given patient's degree of right/left sided heart failure and pulmonary hypertension.

In prior art devices, the use of a pressure reference in a pressure sensing lead produces problems when the devices are intended to be permanently implanted. As noted above, typical piezo-electric sensors suffer from baseline drift. This results in a variable direct current offset being added to the ventricular pressure waveform even when a pressure reference is built into the device.

A device disclosed in U.S. Pat. No. 4,774,950 to Cohen seeks to overcome the shortcomings of the common forms of pacemakers by relying on the mean RVP, mean arterial pressure, mean left atrial pressure, mean left ventricular pressure and/or mean central venous pressure as indicators of haemodynamic compromise. The background to this invention can be found in Cohen et al.'s article "Haemodynamic Responses to Rapid Pacing: A Model for Tachycardia Differentiation.", PACE 11: 1522-1528 (1988).

The Cohen patent discloses a device that either uses discrete circuitry or a microprocessor to perform its functions.

The use of a microprocessor in a pacemaker is not uncommon. However the manipulations described are expensive in the use of both power and microprocessor cycle time when implemented in an implantable device. There are simpler measures of haemodynamic compromise that can be used.

It is well recognized that atrio-ventricular (AV) synchrony, cardiac rate and cardiac ejection volume interact to determine cardiac output. In this regard, reference is made to the article by B. N. Goldreyer, "Physiologic Pacing: The Role of AV Synchrony." PACE 5: 613-615 (1982). Of these, the two former are open to manipulation by a bradycardia support pacemaker. A disadvantage of present programmable devices is that they must be reprogrammed should the recipient's condition change. This involves the expense and inconvenience of a visit to a hospital and drastically reduces the ability of the device to respond to changes in the recipient's condition.

It would thus be advantageous for a pacemaker to have the ability to manipulate automatically these and other pacing parameters to guarantee the best possible bradycardia pacing effect.

SUMMARY OF TERMS

ATP—Antitachycardia pacing

ECG (Electrocardiograph)—The ECG is strictly speaking, the graphical representation of the electrical activity of the heart. However, the term ECG is used loosely to refer to the electrical activity of the heart. The electrical activity of the heart can be sensed either on the surface of the skin, or, on or in the heart.

L (Left)—Used to signify that an acronym refers to the left side of the heart as in: LVFPPA Left ventricular filtered peak-to-peak amplitude (VFPPA); LVP Left ventricular pressure (VP); LVPPF Left ventricular peak pressure function (VPPF); etc.

R (Right)—Used to signify that an acronym refers to the right side of the heart as in: RVFPPA Right ventricular filtered peak-to-peak amplitude (VFPPA); RVP Right ventricular pressure (VP); RVPPF Right ventricular peak pressure function (VPPF) etc.

VF Ventricular fibrillation
VFPPA Ventricular filtered peak-to-peak amplitude
VP Ventricular pressure
VPPF Ventricular peak pressure function
VT Ventricular tachycardia

TERMINOLOGY

A pacemaker is any device capable of electrically stimulating the heart to contract. Most such devices can also sense the electrical activity of a contracting heart and react to alterations in its electrical function. Most such devices are implanted and, if programmable, are interacted with via a telemetric link.

Rate responsive or physiological pacemakers are pacemaking devices that are able to sense and respond to some indicator of increased tissue oxygen demand; for example, respiratory rate. They respond by altering the paced heart rate to meet the changes in oxygen requirements.

A cardioverter/defibrillator is any device that can sense the presence of tachyarrhythmias and deliver an electric shock to a heart in order to revert it back to a normal rhythm. The difference between a cardioverter and a defibrillator lies only in the amount of energy delivered to the heart. Cardioversion is usually used to refer to low energy shocks and defibrillation to high energy shocks. A cardioverter/defibrillator is usually capable of supplying energies in a range of less than 1 Joule to more than 40 Joules. These shocks may or may not be synchronized with the R wave of the ECG.

A cardioverting/defibrillating pacemaker is a device that can perform both cardioverting/defibrillating and pacemaking functions. When referred to herein it also applies to devices that deliver their energy synchronously with a detected R-wave and to devices that do not. When used the term will usually apply to devices that electrically sense/stimulate via electrodes in the right ventricle and atrium but may also apply to devices that do so only in the right ventricle, in the right atrium alone, in multiple heart chambers, via epicardial patches or leads, or via other sense/stimulation configurations.

Antitachycardia pacing (ATP) is a technique implemented in some pacemaking devices. It is directed toward pacing a rapidly and abnormally beating heart back into a more normal rhythm. Its use implies that the tachyarrhythmia detected is considered not to be so sufficiently haemodynamically compromising that it will endanger vital organs within the anticipated treatment time.

ATP may produce a more malignant tachyarrhythmia; for example ventricular tachycardia (VT) may be paced into ventricular fibrillation (VF). For this reason ATP is normally implemented only when there is the option to use cardioversion/defibrillation therapy.

Herein wherever reference is made to a device that senses the right ventricular ECG (RVECG), and/or right atrial ECG, and the right ventricular pressure (RVP), the latter to derive the right ventricular FPPA (RVFPPA) and VPPF (RVPPF), and that uses this information to implement bradycardia pacing, antitachycardia pacing or defibrillation, it should be understood that the device can also sense and respond to the left ventricular ECG, and/or atrial ECG, and VP in a similar fashion, ie via deriving the LVFPPA and LVPPF.

SUMMARY OF THE INVENTION

The present device uses two simple manipulations of the right ventricular pressure signal to overcome the above mentioned shortcomings; i.e. the RVFPPA and the RVPPF. Filtering the RVP signal removes the effect of baseline wander in the transducer. It also tends to remove the effect of heart failure upon the mean value of the RVP. It is well known that the mean RVP and especially the baseline RVP increase with the degree of pulmonary hypertension and/or left sided heart failure. The peak pressure function used is the integration of the filtered RVP waveform. Research has shown that both the RVFPPA and the RVPPF can accurately discriminate haemodynamically compromising tachyarrhythmias.

An object of the invention is to prevent unnecessary discharges to the heart, thereby preventing damage to the myocardium, avoiding causing distress and pain to the recipient and maximizing battery life.

A further object of the invention is to use the RVFPPA or the RVPPF, as well as rate criteria derived from sensing the electrical activity of the heart, as an integral part of the algorithms for the initiation of bradycardia pacing, antitachycardia pacing and defibrillation therapies; i.e. to allow the distinguishing of the different forms of arrhythmia.

Another object of the invention is to switch to the best mode of pacing for a given cardiac state by sensing the right ventricular filtered peak-to-peak amplitude (RVFPPA) and/or the right ventricular peak pressure function (RVPPF), as well as the electrical activity of the right ventricle (RVECG).

In one embodiment of the invention, the values of RVPPF and RVFPPA, and the electrical activity of the heart are continuously monitored and the appropriate therapy initiated whenever an abnormality is detected. In a second embodiment of the invention the RVPPF or the RVFPPA are derived when the electrical activity of the heart indicates some form of malfunctioning and also at a regular interval to monitor any change in the RVP, thus extending battery life.

A further object of the invention is to allow the programming of reference values of RVFPPA and RVPPF, as well as rate criteria derived from sensing the electrical activity of the heart, that are specific to a given recipient of the device.

Another object of the invention is to effect the implementation of a pacing optimization algorithm.

Yet another object of the invention is to respond to a change in RVP, as derived in terms of the RVFPPA and/or RVPPF and or other mechanisms, by altering the A-V delay, the stand-by rate and other pacing parameters to maximize the RVP. Such an altering of pacing parameters is possible, in the absence of a tachycardia, provided a change in RVP occurs to below programmed levels outside those considered optimal, but not sufficiently different from normal to initiate other therapies.

In a second embodiment of the invention the RVP is periodically evaluated. If it is found to be outside preprogrammed values and a tachycardia or other cardiac dysfunction is not co-existent, then continuous monitoring occurs and the microcomputer based pacemaker reverts to the sensing mode of the first embodiment before implementing the pacing optimization algorithm.

The invention described herein functions equally as well sensing pressure from either ventricular chamber and the ECG from any endocardial or epicardial site. The clinical use of the device with its sensors in the left ventricle will differ only in the site of sensor placement and in the reference values programmed into the device by the clinician at implant.

According to the invention, the filtered peak-to-peak amplitude of the ventricular pressure waveform (VFPPA) is obtained after filtering out any voltage offset to the pressure waveform with a highpass filter (preferably having a 3 dB point in the range of 0.1 Hz to 0.5 Hz) and is therefore a measure of the difference between the systolic and diastolic pressures in the ventricle. The ventricular peak pressure function (VPPF) is the integral of the filtered and rectified VP waveform. It is a measure of the work performed by the heart in producing the increase in pressure seen with each contraction The VFPPA and the VPPF are both measures of the contractile performance of the heart and are therefore both measures of haemodynamic compromise.

The manipulations described above reflect only the pulsatile performance of the ventricle. They have the advantage of removing the effect of baseline transducer drift. They also remove the loading effect that a failing left ventricle can have on the right ventricle. Failure of the left ventricle causes the pooling of blood in the lungs and a greater load on the right ventricle. This is reflected by an increase in the mean RV pressure rather than the pulse pressure.

Furthermore the RVFPPA and RVPPF can be intermittently monitored and compared against programmed reference values without the requirement of constant monitoring to obtain long term reference values.

BRIEF DESCRIPTION OF THE DRAWINGS

Further objects, features and advantages of the invention will become apparent upon consideration of the following detailed description in conjunction with the drawings in which.

DETAILED DESCRIPTIONS OF THE DRAWINGS

While the present invention may be implemented using a single chamber or dual chamber implantable cardioverting/defibrillating pacemaker, for purposes of illustration, it is described with respect to a dual chamber device.

Figures 1, 2:
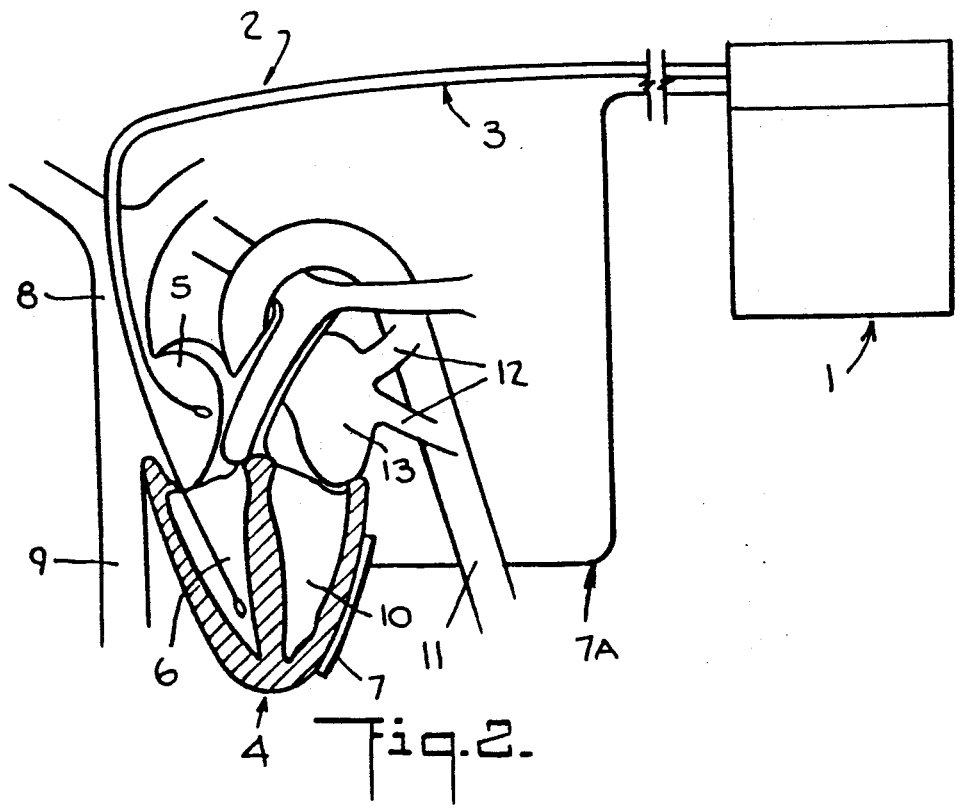
FIG. 1 is a table specifying the therapy to be applied, in accordance with the invention, for representative pulse rate, RVFPPA and RVPPF values.
FIG. 2 is a schematic diagram of the apparatus of the invention in situ.

Referring to FIG. 1, the type of therapy that is typically selected, in accordance with the invention, is set forth as a function of heart rate, RVPPF and RVFPPA. Heart rate is expressed in beats per minute. RVPPF and RVFPPA are expressed as a percentage of resting value. It should be noted that the values given in FIG. 1 are typical percentage values only, and that the values for a given recipient will be determined by electrophysiological studies conducted at the time of implantation.

FIG. 2 schematically illustrates the manner in which an apparatus 1, according to the invention, is provided as an implantable device in a manner similar to that commonly employed for permanently implanted pacemaking defibrillators. Leads 2 and 3 are inserted into the chambers of the heart including, respectively, the right atrium 5 and the right ventricle 6. Lead 3 is a dual ECG/VP lead placed to acquire the electrogram of and the pressure in the right ventricle 6. Apparatus 1 may use one or more epicardial defibrillation patches 7 connected to apparatus 1 by a lead 7A. The break in leads 2,3 and 7A signifies that apparatus 1 is to be implanted at a site removed from the cardiac cavity.

Also illustrated in FIG. 2 are the superior vena cava 8, the inferior vena cava 9, the left ventricle 10, the aorta 11, the pulmonary vessels 12 and the left atrium 13.

Figure 3:
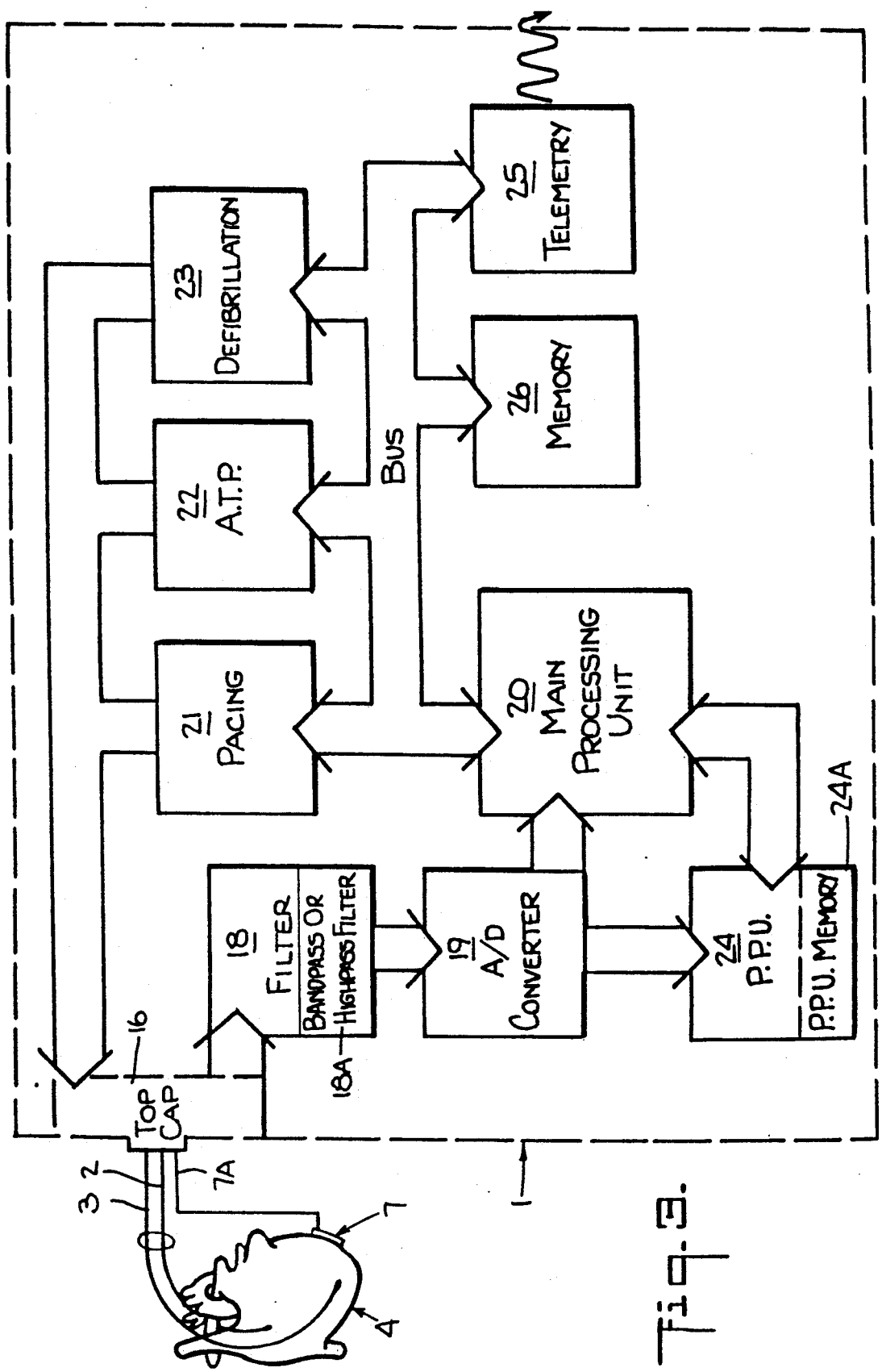
FIG. 3 is a block diagram of the apparatus of the invention.

FIG. 3 schematically illustrates the major circuit and logical units of apparatus 1 and its connection to the heart 4. In the preferred embodiment the heart 4 is connected via the leads 2 and 3 and epicardial patch or patches 7 to the apparatus 1 by a top cap or neck connector 16. The analog signals sensed by the leads are filtered by a filter 18 then converted to a digital format by an A/D converter 19. The VP waveform from lead 3 is filtered with a bandpass or highpass filter 18A portion of filter 18, to remove D.C. offset and low frequency components. The digital signals are then processed by the main processing unit MPU 20 of apparatus 1.

The MPU 20 controls the logic and circuitry of the bradycardia support pacing 21, ATP 22 and defibrillation 23 modules. It can be programmed by a telemetric link 25 and has random access to data storage registers of a memory 26.

The digital signals from the pressure sensing lead are processed by a pressure processing unit P.P.U. 24 that is illustrated as a separate module, but may also be a logical unit within MPU 20.

Figure 4:
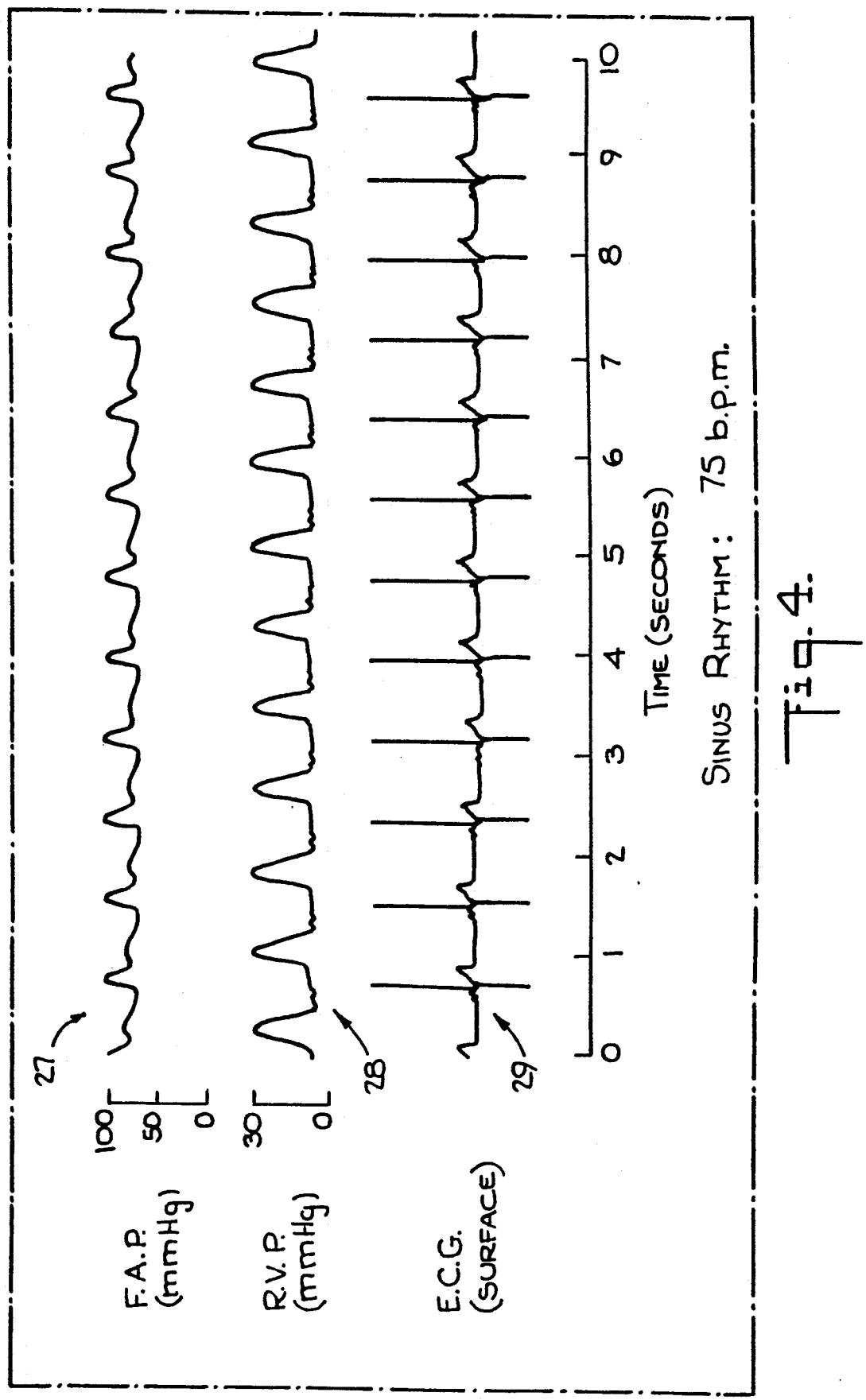
FIG. 4 is a representative diagram of normal femoral artery pressure, right ventricular pressure and E.C.G. waveforms taken from a dog.

FIG. 4 depicts a typical RVP waveform 28. FIG. 4 also depicts the typical form of the pressure wave obtained in the femoral artery, FAP 27, and a surface ECG 29. It can be seen that the modulations of both pressure waveforms fall in time between the R waves of the ECG.

Figure 5:
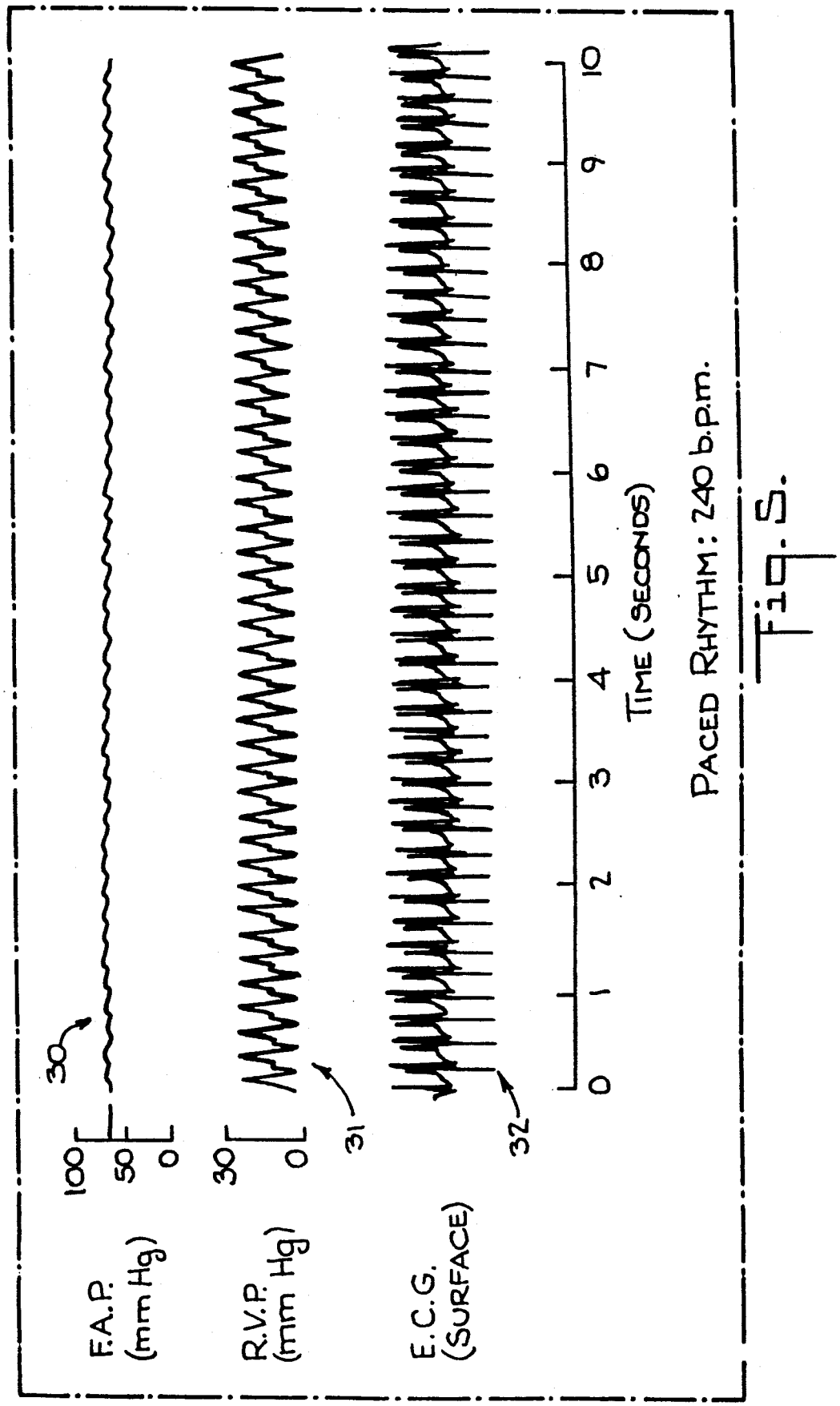
FIG. 5 is a representative diagram of femoral artery pressure, right ventricular pressure and E.C.G. waveforms during ventricular pacing at 240 b.p.m. in the dog.

FIG. 5 shows that the peak-to-peak amplitude of the RVP 31 is well maintained even when the heart is paced to a high rate. It can also be seen that the FAP 30 at this rate is low, but is still life sustaining in the short term. It can also be seen that the peaks of the pressure waveform in the ventricle and the femoral artery both occur after the R wave of the surface ECG 32.

Figure 6:
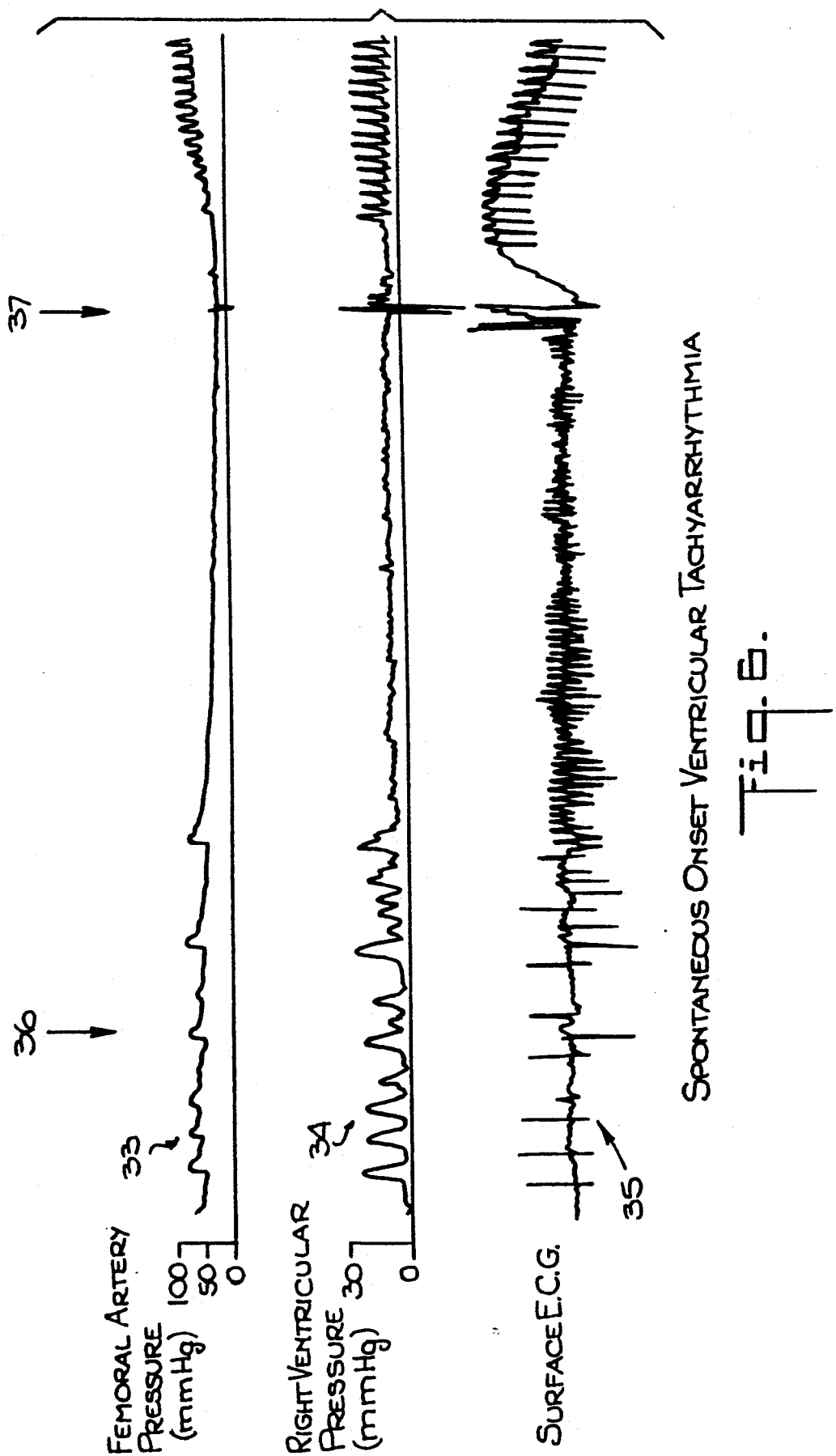
FIG. 6 is a representative diagram, taken from a dog, of femoral artery pressure, right ventricular pressure and E.C.G. waveforms during an episode of ventricular fibrillation.

FIG. 6 depicts the typical changes in FAP 33, RVP 34 and surface ECG 35 with the onset of ventricular fibrillation at 36. There is almost no modulation in either the FAP 33 or RVP 34 waveforms during well established VF and the FAP 33 is so low that life would cease unless prompt action were taken. Normal function is returned after the administration of a defibrillating shock at 37.

The processing unit for the pressure waveform, PPU 24 in FIG. 3, derives the FPPA and VPPF from the filtered and digitized VP waveform. The PPU 24 communicates the derived data to the MPU 20. The MPU 20 has access to the data registers of a P.P.U. memory 24A of the PPU 24.

The RVFPPA is obtained by filtering the VP waveform with a highpass filter with a −3 db frequency in the range of 0.1 to 0.5 Hz. In the preferred embodiments this filter is a second order Butterworth filter. The RVFPPA is derived from the filtered RVP waveform by determining the maximum excursion of the filtered signal over a defined time period. In the preferred embodiment this time period is determined by the period between R waves in the intracardiac ECG. The RVPPF is obtained by rectifying the filtered RVP waveform and then integrating it. The integral for each contraction is obtained by reference to the R wave interval from the endocardial ECG. In the preferred embodiments of this device both these signals are used to determine whether or not the recipient of the device is haemodynamically compromised.

The device has two main implementations each of which can be implemented using one of two algorithms. In the first algorithm (hereafter referred to as the "simple threshold algorithm") the RVFPPA is monitored and compared to a threshold value. This value can be programmed as either an absolute value or as a percentage of a long term mean of the RVFPPA.

The threshold detector is linked to a simple counter. Each time the value of the RVFPPA becomes greater than the threshold value a counter is reset to zero. This counter increments each time the RVFPPA is sensed to be less than the threshold value. If this counter reaches a pre-programmed value then haemodynamic compromise is deemed to exist. In the normally functioning recipient of this device the rising edge of the RVFPPA periodically resets the counter before the triggering value is reached. When the counter reaches the triggering level, the PPU 24 communicates this to the MPU 20 indicating that a state of haemodynamic compromise exists.

In the second algorithm (hereafter referred to as the "X out of Y algorithm"), the RVFPPA is assessed with each cycle as the sum of the greatest negative and positive digital values obtained over one cycle. The value is manipulated as a percentage of a programmed reference value and the values for the last Y beats are stored in memory, where Y is a programmed value. The RVPPF value is calculated as a percentage of a programmed value and the values for the last y beats are also stored in memory.

If X out of the last Y beats, where X and Y are programmed values, fail to produce RVFPPA and/or RVPPF values above programmed levels, then the PPU 24 communicates this to the MPU 20 thus indicating that a state of haemodynamic compromise exists. The simplest case of this X out of Y test is with both X and Y equal to one. The average of the stored values is then used, in conjunction with information gained electrically about the heart rate, to determine what therapy to initiate as per FIG. 1. If apparatus 1 senses an electrical disturbance of the heart, then the MPU 20 interrogates the PPU 24 as to the haemodynamic state of the recipient of apparatus 1 to determine what therapy to initiate as per FIG. 1.

In a second embodiment of the invention, if apparatus 1 senses an electrical disturbance of the heart, then the MPU 20 activates the PPU 24 to derive the RVFPPA and RVPPF values and performs an X out of Y test as described above. Therapy is then initiated as per FIG. 1. No therapy will be initiated if there is no evidence of haemodynamic compromise. The MPU 20 also periodically activates the PPU 24 to ensure that the FPPA and VPPF are within optimal normal limits. If the FPPA and VPPF are not within normal limits, then the MPU 20 will initiate a pacing optimization algorithm as described below.

Thus, in both embodiments a fall in the RVFPPA and/or RVPPF, in the absence of a tachyarrhythmia, initiates a bradycardia support pacing optimization algorithm. Apparatus 1 may manipulate the A-V delay, paced heart rate and/or other pacing parameters to maximize the VP. As described below, it is principally implemented to manipulate A-V delay and heart rate. However since the manipulations involved are generally microprocessor based, any other programmed parameter can also be manipulated.

Thus, for both detection algorithms, the presence of a bradycardia is defined in terms of an electrically sensed bradycardia with or without the pressure sensor detecting haemodynamic compromise. Asystole is defined in terms of the absence of electrical activity and of modulation in the RVFPPA.

The invention can be implemented in one of the two embodiments using either of the sensing modes described above. In the first embodiment the FPPA or VPPF are continuously derived. In the second embodiment the haemodynamic sensor is activated only when an electrical abnormality in the function of the heart is detected.

In the first embodiment the MPU 20 continuously monitors the PPU 24 as well as the electrical activity of the heart. The result of the haemodynamic compromise detection algorithm is used in conjunction with information gained electrically about the heart rate, to determine what therapy to initiate. Since both electrical and haemodynamic function of the heart are being continuously sensed, an abnormality in the function of either can initiate therapy. In this embodiment the pacing optimization algorithm is continuously active during bradycardia support pacing.

It is noteworthy that a dual chambered configuration allows the use of lower energy cardioversion shocks to revert atrial fibrillation that is haemodynamically compromising. This arrhythmia is recognized by the presence of an atrial rate that is higher than the ventricular rate in the presence of haemodynamic compromise.

Figure 7:
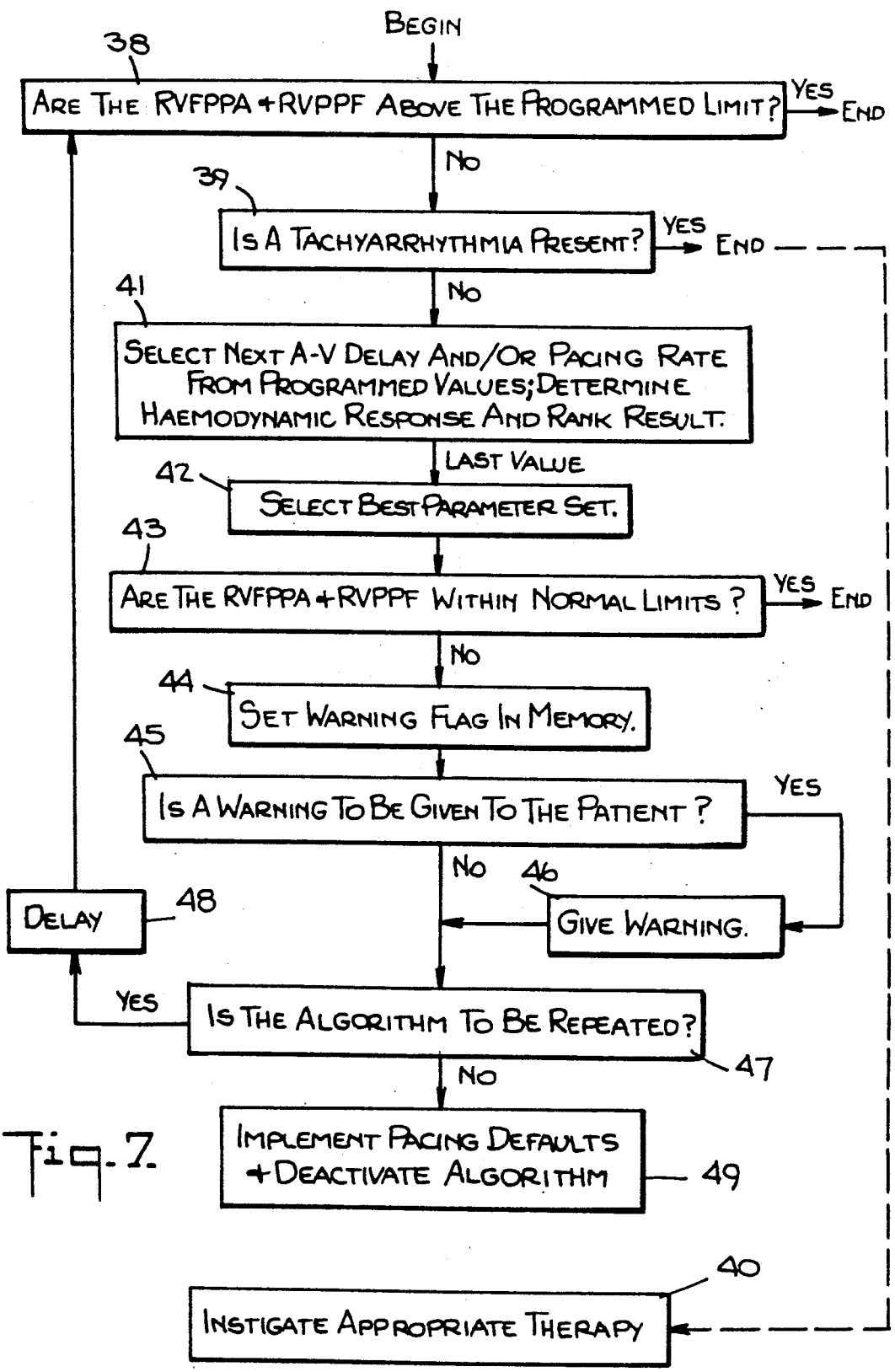
FIG. 7 is a flow chart representing the logic used in the bradycardia support pacing optimization algorithm in accordance with the invention.

FIG. 7 illustrates the logic behind the pacing optimization algorithm. This algorithm is designed to function with existing technologies; in particular with existing bradycardia support pacing, anti-tachycardia pacing and cardioverting/defibrillating therapies. The devices and/or logic blocks needed to implement these therapies in hardware or software are well known in the art.

With specific reference to FIG. 7, the first decision, at step 38 is whether or not one of the RVFPPA or RVPPF are within the programmed limits. If so, the program ends and eventually again returns to step 38. If not, then the presence of a tachy-arrhythmia is tested for at step 39. If a tachy-arrhythmia is present, the appropriate therapies are instituted at 40. In the preferred embodiments, the selection of which therapy is to be used is based on heart rate and haemodynamic parameters (FIG. 1).

In the absence of a tachyarrhythmia, whether or not bradycardia support pacing is already functioning, an optimization algorithm is initiated at 41 and the device begins to automatically alter pacing parameters. The parameters to be manipulated are specified by the clinician at implant of the device, or later via the telemetric link, and vary with the nature of the pacing strategies implemented in the device. If pacing is not already in operation, then the programmed stand-by rate is used as the starting point of the algorithm.

In both embodiments of the device the paced heart rate is varied within programmed upper and lower limits by sweeping up from the lowest rate to the highest rate in 5 b.p.m. steps. The range of values open to the clinician is 30-200 b.p.m. The clinician has the option to use any or all of the values in this range, to nominate the order in which they are used, and the starting and finishing point values.

For dual chamber devices the A-V delay is varied within programmed upper and lower limits by sweeping up from the lowest rate to the highest rate in 20 millisecond steps. The range of values open to the clinician is 0-500 milliseconds. The clinician has the option to use any or all of the values in this range, to nominate the order in which they are to be used and the starting and finishing point values.

The clinician also has the option to specify the precedence in which parameters are to be altered as well as the delay period between each change. However, in the preferred embodiment of the invention the procedure is to sweep through each value of A-V delay in the programmed range, then select the next heart rate value in the programmed range, then sweep the A-V delay range again, etc. until the full range of both parameters has been swept and the point of maximal function obtained. The parameters that produce the best haemodynamic result are then selected at step 42.

The function of the optimization algorithm is reinstituted after a programmed time has elapsed as determined at step 48, if a sub-optimal haemodynamic state still exists as determined by step 43. If the haemodynamic state has been optimized so as to be within acceptable limits, the program ends and eventually starts again at step 38. If the haemodynamic state is still suboptimal, the fact that this has occurred will be stored in the memory of the microprocessor of MPU 20 at step 44. On the next occasion that the device is accessed via the telemetry link, this information will be available to the clinician.

The apparatus has the capacity to warn the patient of the failure of the pacing optimization algorithm. This facility is capable of being activated or inactivated by the clinician via the telemetric link 25. A determination of whether the apparatus has been programmed to do so is made at step 45. If it has been so programmed, it will trigger a tactile warning to the patient at step 45 by way of a piezo-electric vibrating device attached to the inside of the can containing the apparatus.

The clinician has the option to program the number of consecutive attempts that the device may make in trying to establish a stable haemodynamic state to thereby control the determination made at step 47. The clinician may also specify a set of default pacing parameters to be implemented at step 49, once this number of attempts has been made. If this should occur the algorithm cannot be reactivated except via the telemetric link.

The logic for the algorithm is implemented via software. In practice apparatus 1 is implanted and a series of electrophysiological studies are performed to guide the clinician in the choice of programmed variables. In particular, the resting state values of the patient's VFPPA and VPPF must be obtained. Thus the performance of the apparatus can be maximized before the patient is discharged.

The invention also may be implemented as a rate responsive pacemaker using open loop control based upon respiration. In such a device, the algorithm is interrupted whenever a change in respiratory rate indicates that a change in heart rate is required. It is not re-instituted until a stable respiratory rate is again attained.

Although the invention has been described with reference to particular embodiments, it is to be understood that these embodiments are merely illustrative of the application of the principles of the invention. Numerous modifications may be made and other arrangements may be devised without departing from the spirit and scope of the invention.

What is claimed is:

1. An apparatus for the treatment of the heart, comprising:
   a) means for obtaining an electrogram from the heart;
   b) means for acquiring a signal indicative of ventricular pressure;
   c) processing means for processing said signal to produce a signal representative of at least one of filtered peak-to-peak ventricular pressure amplitude and ventricular peak pressure function, the latter comprising the integral of a filtered and rectified ventricular pressure waveform signal;
   d) comparison means responsive to said representative signal for determining whether at least one of said filtered peak-to-peak ventricular pressure amplitude and said ventricular peak pressure function is below a predetermined level;
   e) examining means for examining said electrogram to determine whether an arrhythmia is present;
   f) therapy selection means responsive to said comparison means and said examining means for selecting therapy to apply to the heart if at least one of said filtered peak-to-peak ventricular pressure amplitude and said ventricular peak pressure function is below said predetermined level and an arrhythmia is present; and
   g) therapy application means for applying a therapy to the heart.

2. The apparatus of claim 1 wherein said processing means includes means for removing changes in baseline level of said signal indicative of ventricular pressure.

3. The apparatus of claim 1 wherein said processing means includes means for removing low frequency components in said signal indicative of ventricular pressure.

4. The apparatus of claim 3, wherein said means for removing low frequency components is a high pass filter.

5. The apparatus of claim 4, wherein said high pass filter has a $-3$ dB point in the range of 0.1 to 0.5 Hz.

6. The apparatus of claim 3 wherein said means for removing low frequency components is a bandpass filter.

7. The apparatus of claim 1, wherein said processing means comprises:
   filter means for filtering said signal indicative of ventricular pressure to produce a filtered signal;
   rectifier means for rectifying said filtered signal to produce a rectified signal; and
   integration means for integrating the filtered, rectified signal to produce said ventricular peak pressure function.

8. The apparatus of claim 1, wherein said processing means comprises:
   filter means for filtering said signal indicative of ventricular pressure to produce a filtered signal;
   means for determining a minimum value of said filtered signal;
   means for determining a maximum value of said filtered signal; and
   means for determining a difference between said minimum value and said maximum value to define a peak-to-peak amplitude of said filtered signal, whereby said processing means produces a signal representative of said filtered peak-to-peak ventricular pressure amplitude.

9. The apparatus of claim 1, wherein said electrogram and said ventricular pressure are continuously sensed; and wherein said processing means continuously produces said representative signal.

10. The apparatus of claim 1, wherein said electrogram is continuously sensed, and wherein said processing means produces said representative signal only when an arrhythmia is indicated by the electrogram.

11. The apparatus of claim 1, wherein said therapy selection means responds to a bradycardia, and said therapy means includes a pacing means and a pacing optimization algorithm for optimizing pacing so as to produce an increase in at least one of filtered ventricular peak-to-peak pressure amplitude and ventricular peak pressure function.

12. The apparatus of claim 10, wherein said pacing optimization algorithm selects various values of heart rate and A-V delay.

13. The apparatus of claim 1, wherein said comparison means comprises a counter responsive to amplitude of said representative signal, said counter being reset if said amplitude reaches a predetermined level, said counter counting up if said amplitude does not reach a predetermined level; and means for ascertaining when the count in said counter reaches a predetermined value, and to then provide an input to said therapy selection means indicating that therapy is required.

14. The apparatus of claim 1, wherein said comparison means comprises: means for storing values of amplitude of representative signals derived from Y successive heart beats, and means for determining whether X of the stored amplitudes are below a predetermined value; and to then provide an input to said therapy selection means indicating that therapy is required.

15. An apparatus for the treatment of a malfunctioning heart comprising:
   a programmable device capable of sensing malfunction of the heart and the successful treatment of malfunction based on electrical and haemodynamic function of the heart;
   means for calculating a filtered peak-to-peak amplitude and a filtered and rectified integration of a pressure waveform of the right ventricle;
   means for determining haemodynamic compromise based upon the calculations;
   first therapy means for initiating anti-tachycardia pacing and cardioversion/defibrillation based on the electrical and haemodynamic function of the heart; and
   second therapy means for implementing a method of bradycardia support pacing optimization based on both the electrical and the haemodynamic function of the heart.

16. The apparatus of claim 15 further comprising means for warning at least one of a recipient of the device and the recipient's clinician of failure of said method.

17. The apparatus of claim 15 wherein at least one of the pressure waveform of the left ventricle, the right atrium and the left atrium is used instead of, or in conjunction with, that of the right ventricle.

18. The apparatus of claim 15 wherein sensing of electrical activity of the heart and electrical stimulation of the heart is done in at least one of the right atrium, the right ventricle, the left atrium and the left ventricle.

19. The apparatus of claim 15 wherein said second therapy means is rate responsive.

20. A method of determining an index of the hemodynamic function of the heart by monitoring right ventricular pressure to obtain a pressure waveform comprising the steps of: high-pass filtering the pressure waveform and determining the peak-to-peak amplitude from the filtered pressure waveform to determine an index of hemodynamic function; or, filtering and rectifying said pressure waveform and then integrating the filtered and rectified waveform to produce a peak pressure function representative of said hemodynamic index.

21. The method of claim 20, wherein said monitoring is implemented continuously.

22. The method of claim 20, wherein said monitoring is implemented intermittently.

23. The method of claim 20 wherein a pressure waveform of at least one of the left ventricle, the right atrium and the left atrium is used instead of, or in conjunction with, that of the right ventricle.

24. A method of automatically optimizing bradycardia support pacing by monitoring the haemodynamic performance of the heart comprising the steps of:
   sensing the haemodynamic state of the heart by monitoring right ventricular pressure, wherein said step of sensing the haemodynamic state further comprises processing the right ventricular pressure waveform by either high-pass filtering said pressure waveform and determining the peak-to-peak amplitude of said filtered pressure waveform; or, filtering and rectifying said pressure waveform and then integrating the filtered and rectified waveform to produce a peak pressure function
   determining that the sensed haemodynamic state is outside programmed performance limits, that there is a relatively steady cardiac state present, and that there is not a tachyarrhythmia present;
   sweeping through programmed pacing parameter values including at least one of A-V delay and pacing rate in a step wise pattern;
   reassessing the heart's haemodynamic state and electrical activity after each change in pacing parameters; and
   choosing, out of those pacing parameters tested, ones that produce the best haemodynamic state.

25. The method of claim 24 further comprising warning at least one of a recipient of the device and the recipient's clinician of failure of the method.

26. The method of claim 24 wherein said monitoring is implemented continuously.

27. The method of claim 24 wherein said monitoring is implemented intermittently.

28. The method of claim 24 wherein a pressure waveform of at least one of the left ventricle, the right atrium, and the left atrium is used instead of, or in conjunction with, that of the right ventricle.

* * * * *